(12) United States Patent
Hansen et al.

(10) Patent No.: US 7,037,948 B2
(45) Date of Patent: *May 2, 2006

(54) METHOD FOR INCREASING THE PRODUCTION IN AN EXISTING PROCESSING PLANT AND A PROCESSING PLANT

(75) Inventors: Roger Hansen, Trondheim (NO); Jostein Sogge, Stjordal (NO); Bjorn Jarle Veland, Jar (NO); Ola Olsvik, Hundhamaren (NO)

(73) Assignee: Statoil ASA, Stavanger (NO)

( * ) Notice: Subject to any disclaimer, the term of this patent is extended or adjusted under 35 U.S.C. 154(b) by 39 days.

This patent is subject to a terminal disclaimer.

(21) Appl. No.: 10/481,925

(22) PCT Filed: Jun. 27, 2002

(86) PCT No.: PCT/NO02/00235

§ 371 (c)(1),
(2), (4) Date: Apr. 26, 2004

(87) PCT Pub. No.: WO03/002497

PCT Pub. Date: Jan. 9, 2003

(65) Prior Publication Data

US 2004/0198846 A1    Oct. 7, 2004

(30) Foreign Application Priority Data

Jun. 27, 2001   (NO)   ................................. 2001 3226

(51) Int. Cl.
*C07C 27/00*   (2006.01)
(52) U.S. Cl. ...................... 518/705; 518/700; 518/702; 518/703; 518/704; 518/706
(58) Field of Classification Search ................ 518/700, 518/702, 703, 704, 705, 706

See application file for complete search history.

(56) References Cited

U.S. PATENT DOCUMENTS 6,333,014 B1 * 12/2001 Filippi ........................ 423/359
6,794,418 B1 *  9/2004 Sogge et al. ................ 518/706

FOREIGN PATENT DOCUMENTS

WO       WO 01/47846 A1 *  7/2001

* cited by examiner

*Primary Examiner*—J. Parsa
(74) *Attorney, Agent, or Firm*—Kirkpatrick & Lockhart Nicholson Graham LLP (57) ABSTRACT

A method of increasing the production in an existing process plant for converting natural gas into a product, where the natural gas is first converted to a synthesis gas in a synthesis gas section, the synthesis gas is brought to reaction in a reactor for synthesis of the product, where non-converted synthesis gas and product are separated into two streams, where a product-rich stream is taken off the process, while a product-poor stream is re-circulated back as feed to the reactor together with fresh synthesis gas, and where part of the re-circulating stream is taken off the re-circulation loop as a purge gas, where the purge gas is separated into hydrogen-rich and hydrogen-poor streams, where hydrogen-rich streams are introduced in stages of the process where addition of hydrogen is desirable, and where the residual thermal value of the hydrogen-poor stream may be used for heating prior to the stream being discharged, wherein the synthesis gas from the synthesis gas section receives a hydrogen-rich stream from the separated purge gas, and that this hydrogen enriched synthesis gas is passed through a new flow reactor for production of product, and also a unit for separating a product-rich stream that is taken off, and a product-poor stream used as feed to the original reactor, and that the product-poor stream, which is used as feed to the original reactor, receives additional synthesis gas produced in a separate secondary synthesis gas line, is described. Additionally, a process plant for carrying out the method is described.

16 Claims, 2 Drawing Sheets

METHOD FOR INCREASING THE PRODUCTION IN AN EXISTING PROCESSING PLANT AND A PROCESSING PLANT

The present invention concerns a method of increasing the production in an existing process plant, and a process plant that has been modified in order to implement the method.

Today, there is a clear tendency when building new process plants such as plants for production of methanol from natural gas or other suitable carbon sources, to build plants with increasingly greater production capacity, e.g. of more than 5000 tons of methanol per day. By so doing, the production costs are reduced due to scale factors.

In areas with a low price on natural gas, methanol may be produced at a cost of down to USD 80 per ton, which allows methanol to gain entry to a fuel market, i.e. to fuel cell cars and electric power production.

For existing process plants that are too small according to today's requirements, there is a demand for solutions whereby the total production may be increased, thus reducing the production costs pr. unit, without having to carry out major, expensive alterations and replacements of the existing process plant.

Methods of producing methanol are known from prior art, which make it possible to achieve a simpler and more reasonable plant, an increased yield or a certain increase in production when compared with a conventional methanol production plant.

Thus it is an object of the present invention to provide a method of increasing the production of an existing plant without having to carry out major, expensive alterations of the existing plant; and also a process plant that has been modified in order to implement the present method.

This is achieved according to the present invention by a method of increasing the production of an existing process plant for conversion of natural gas into a product, where the natural gas is first converted into a synthesis gas in a synthesis gas section, the synthesis gas is brought to react in a reactor for synthesis of the product, where non-converted synthesis gas and product are separated into two streams, where a product-rich stream is drawn out of the process, while a product-poor stream is re-circulated back as feed to the reactor along with fresh synthesis gas, and where part of the re-circulating stream is taken off the re-circulation loop as a purge gas, where the purge gas is separated into hydrogen-rich and hydrogen-poor streams, where hydrogen-rich streams are introduced in stages of the process where the addition of hydrogen is desirable, and where the residual thermal value of the hydrogen-poor stream may be used for heating prior to discharge, where the synthesis gas from the synthesis gas section receives a hydrogen-rich stream from the separated purge gas, and that this hydrogen enriched synthesis gas is passed through a new flow reactor for production of the product and a unit for separation of a product-rich stream that is taken off, and a product-poor stream that is used as feed to the original reactor, and that the product-poor stream used as feed to the original reactor receives additional synthesis gas produced in a separate secondary synthesis gas line.

According to a preferred embodiment, the separate secondary synthesis line comprises a steam reformer.

According to another preferred embodiment, the new synthesis gas line also comprises a pre-converter, and that the flow from the pre-converter is separated into a product-rich fraction that is passed to a section for purification of the product, and a product-poor stream that is introduced into the original synthesis loop.

Preferably, hydrogen enriched synthesis gas from the original synthesis gas section and/or gas from the re-circulation loop in the original synthesis section is drawn off and introduced into the new synthesis gas line upstream of the pre-converter.

Preferably, the product produced through the method is methanol or dimethyl ether.

A process plant is also provided for production of a product based on natural gas, where the process plant comprises a synthesis gas section for production of synthesis gas consisting mainly of CO, $CO_2$, $H_2$ and water, a synthesis section in which the product is formed, and also a purification section in which the product is separated from non-converted reactants and other materials and purified, where non-converted reactants that are separated from the product are re-circulated to the synthesis section, and where some of the re-circulated gas is taken off in a line in order to prevent accumulation of inert gases, the plant also comprising a separation unit for separating the gas that is taken off in a line, into hydrogen-rich and hydrogen-poor fractions, a line for optionally leading hydrogen-poor fractions to combustion and lines for leading hydrogen-rich fractions into the natural gas feed and for re-circulation to the synthesis section, respectively, where a flow reactor is disposed between the synthesis gas section and the synthesis section for synthesis of the product, and also a separation unit for separation of a product-rich fraction to a line and a product-poor fraction to a line leading to the synthesis section, and a separate secondary synthesis gas line is provided for production of secondary synthesis gas, along with a line for feeding the secondary synthesis gas to the synthesis reaction.

Preferably, the secondary synthesis gas line comprises a steam reformer.

Preferably, the secondary synthesis gas line also comprises a pre-converter with an outlet for a product-rich stream that is passed to a purification section for the product, and an outlet for a product-poor stream that is introduced into the original synthesis loop upstream of the reactor.

Below, the invention will be described by means of an example and the accompanying figures, in which.

Figure 1:
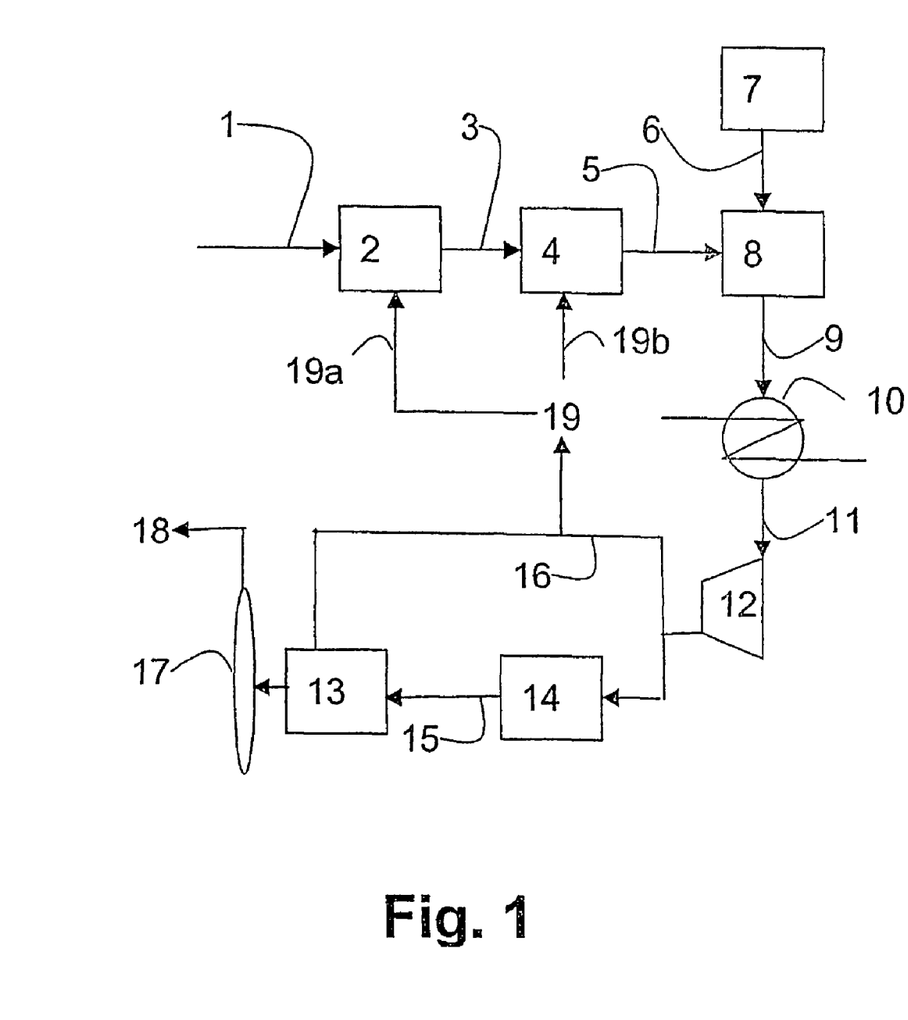
FIG. 1 schematically shows the construction of a conventional plant for production of methanol from natural gas.

In the main, production of methanol today is carried out in accordance with the schematic drawing in FIG. 1. The process plant consists principally of three sections; a synthesis gas section (2, 4, 8) in which synthesis gas is produced, normally based on natural gas (NG), a synthesis section (14) in which the actual synthesis of methanol takes place, and a distillation section (17) in which the produced methanol is purified. The synthesis of methanol takes place through the two following reactions:

1) $CO+2H_2=CH_3OH$, or
2) $CO_2+3H_2=CH_3OH+H_2O$

The synthesis gases, which mainly comprise CO, $CO_2$ and $H_2$, besides water and non-reacted hydrocarbons, are produced according to one of three different concepts, i.e.:
a) conventional steam reforming,
b) conventional autothermal reforming with a catalyst (ATR) or without a catalyst (POX), or
c) a combination of a) and b).

Prior to the natural gas being passed into line 1 to the reformer for synthesis gas production, sulphur compounds are removed in a conventional manner, and steam is then saturated into and/or added directly to the gas. The saturation may also take place through use of a so-called "saturator". Ordinarily, the gas is also treated in a so-called pre-reformer 2 prior to being passed into the reformer 4, 5, in order to convert all higher hydrocarbons.

The following chemical reactions take place during the production of synthesis gas:

3. $CH_4+H_2O=CO+3H_2$, steam reforming
4. $CH_4+1,5O_2=CO+2H_2O$, partial oxidation
5. $CO+H_2O=CO_2+H_2$, shift reaction Reactions 3 and 5 in the reforming reactor are highly endothermic, and the heat required for the reaction may be supplied either through external heating, such as in a steam reformer, or through a combination with partial oxidation according to reaction 4, such as in an autothermal reformer.

In a steam reformer (SR), natural gas (NG) (methane) is converted in a tubular reactor at high temperature and relatively low pressure. A conventional steam reformer consists of a large number of reactor tubes, normally 100 to 1000, with a length of 10–16 m, where each tube has an inner diameter of around 10 cm and an outer diameter of around 12 cm. This unit may have a length of up to 50 meters, a width of more than 10 meters and a height of more than 20 meters, and therefore such a reactor may be relatively space-requiring.

Conventional steam reformers operate in a pressure range from around 15 to 40 bar. The outlet temperature of such a reformer may be close on 950° C. The heat required to drive the reaction is added by means of external heating, and the reformer may be top, bottom or terrace fired. The heat may also be transferred to the reaction by means of convective heat such as in a heat exchanger reactor. The ratio between steam and carbon is from 1.6 to 4, and the ratio between $H_2$ and CO in the product stream from the reformer is around 3. A typical synthesis gas from a conventional steam reformer contains around 3 volume % methane.

In an autothermal reformer (ATR), the synthesis gas production takes place mainly via reactions 3 and 4, so that the heat required for reaction 3 is generated internally by reaction 4. In an ATR, natural gas (methane) is led into a combustion chamber together with oxygenous gas such as air. The temperature of the combustion chamber may reach more than 2000° C. Following the combustion, the reactions are brought into equilibrium across a catalyst before the gases leave the reformer at a temperature of around 1000° C. The dimensions of an ATR may be a height of 10–20 meters with a diameter of around 4–7 meters.

An alternative autothermal reformer makes use of a concept called partial oxidation (POX). Such a reformer does not contain any catalyst for accelerating the reactions, and as such will generally have larger dimensions than an ATR.

Reforming of natural gas may also occur through combined reforming (CR), where the reformer section consists of an SR and an ATR. Combining SR and ATR makes it possible to regulate the composition exiting the reformer section by controlling the admission of the two reformers. In CR, SR is operated at somewhat milder conditions than in the case of normal SR, i.e. at a slightly lower temperature. This results in a slightly higher methane content in the emissions from the reformer. This methane content is converted in the subsequent ATR. For such a reformer, the ratio between carbon and steam lies in the range 1.2 to 2.4, with the ratio between hydrogen and CO in the product gas being well over 2. The optimum stoichiometric number ($SN=(H_2-CO_2)/(CO_2+CO)$) for the synthesis of methanol is around 2.05.

FIG. 1 shows a synthesis gas section of the CR type. However the type of synthesis gas section used in the plant is not critical. A plant with a synthesis gas section of the ATR type will be without SR 4, while a plant of the SR type will have no ATR 8 and air separation unit 7 with associated line 6.

After the synthesis gas section 2, 4, 8, the synthesis gas is carried in line 9 to a heat exchanger 10 in which it is cooled. After the heat exchanger 10, the synthesis gas is carried in line 11 to a compressor 12 in which it is compressed to the desired pressure of the methanol synthesis section, which is typically about 80 bar.

The synthesis of methanol in the synthesis section takes place according to chemical equations 1 and 2 above, and is an exothermic process that traditionally makes use of several different types of reactors 14, such as:

Isothermal tubular reactor with a catalyst on the inside of vertical tubes and boiling water on the outside. The heat of reaction will then be removed through partial evaporation of the water.

Adiabatic fixed bed reactors with interstage cooling.

Fluidized bed reactor.

Adiabatic reactors with cooling through introduction of new feed at several levels down through the reactor (quench converter system).

After the reactor 14, the product is passed via line 15 to a crude methanol separator 13 that separates the product stream into a methanol-rich stream 40 and a methanol-poor stream 16. The methanol-rich stream in line 40 is passed to a conventional methanol purification unit 17 that produces methanol out of line 18.

The methanol-poor stream is normally passed back to the reactor 14 via a re-circulation line 16. Alternatively, the reactor is a flow reactor without re-circulation, followed by one or more similar reactors connected in series.

FIG. 1 shows a synthesis loop 13, 14, 15 and 16. The actual re-circulation loop consists of a heat exchanger ("inter exchanger") (not shown) that pre-heats the feed to the synthesis reactor and cools the production gas; the synthesis reactor(s) 14; a crude methanol separator 13; and a system for recovering energy from the exothermic methanol synthesis reactions (not shown).

A so-called purge stream is taken off this re-circulation loop via line 19 in order to prevent accumulation of inert (non-reactive) gases in the re-circulation loop. The purge gas in line 19 is often split into a first stream 19a that is brought together with the feed gas in the gas feed 1, and a second stream 19b that is used as fuel gas for heat-requiring processes in the methanol synthesis, such as the steam reformer 4, or in another process in the same plant; or it is discharged.

A drawback of this prior art is that inert gases, primarily nitrogen, in the re-circulated purge gas will react with other components of the synthesis gas and convert to $NO_x$ and $NH_3$ under the high temperatures of the reforming plant. According to the present invention, this is avoided through that part of the purge gas which is rich in inert gas being used only as fuel for energy-requiring processes such as the steam reformer 4.

Improved Process For Synthesis of Methanol

Figure 2:
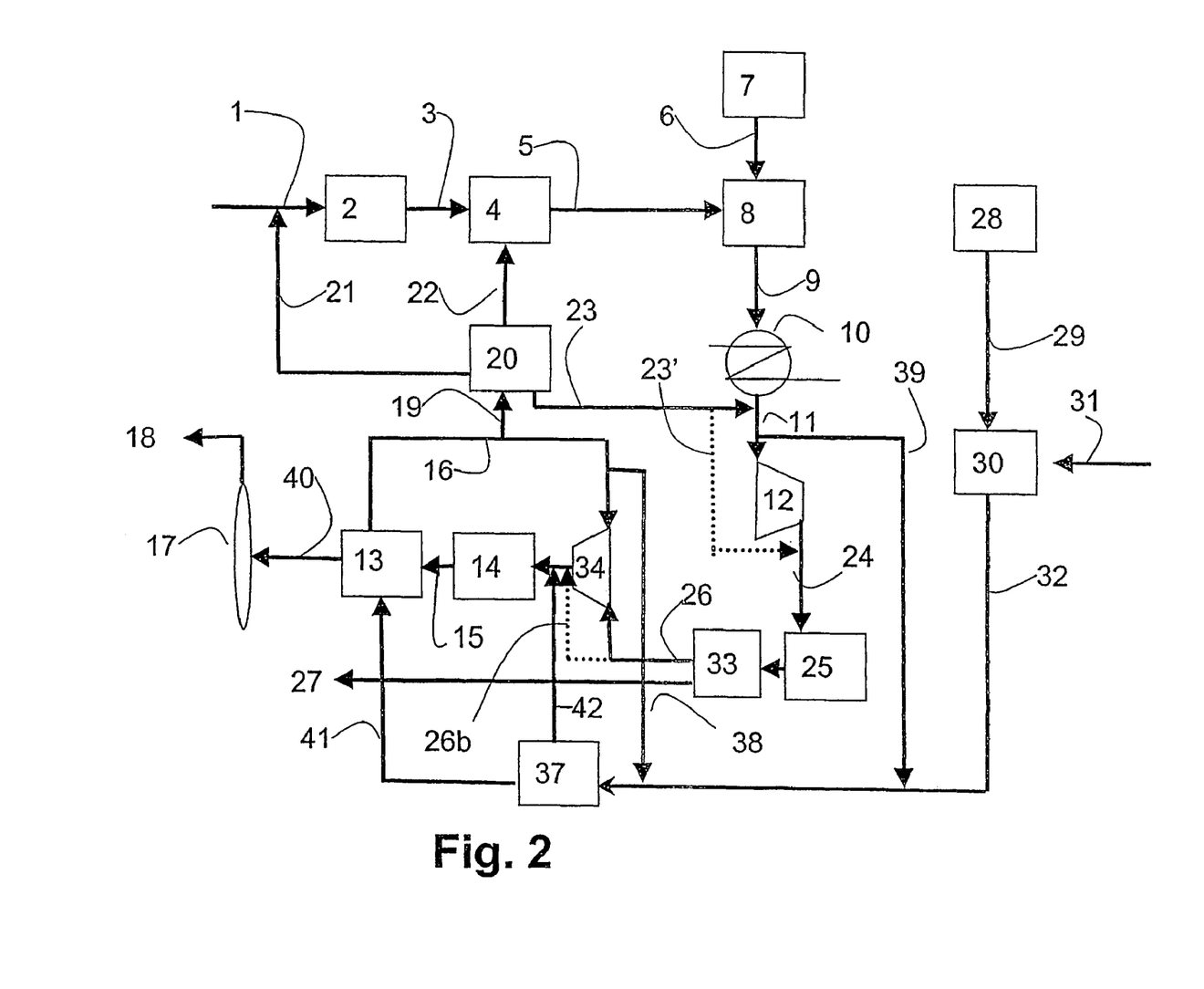
FIG. 2 schematically shows the construction of a plant according to the present invention.

FIG. 2 illustrates a preferred embodiment of the present invention, where a conventional, existing methanol synthesis plant such as described above has been used as a basis, and where this plant has been modified in order to increase the production capacity. A plant with an existing reformer section based on CR was used as a basis.

In this modified plant, equivalent elements have been given the same reference number, and the description is mainly concerned with the differences relative to the original plant.

Purge gas taken off from the re-circulation loop in line 19 is here separated into three streams in a separation unit 20; two hydrogen-rich streams 21, 23 at different pressures, and a hydrogen-poor stream 22. The separation unit 20 is a conventional hydrogen recovery unit that works according to either the Pressure Swing Adsorbtion (PSA)-principle, the membrane principle or is of a cryogenic type. Preferably, the hydrogen-rich fractions have a hydrogen content of 70 to 100%.

One hydrogen-rich stream 21 is led into the gas feed 1 and mixed with the incoming natural gas. The second hydrogen-rich stream 23 is led into the synthesis gas stream in line 11. Alternatively, and depending on the relative pressures of the various parts, this hydrogen-rich stream 23 may be led via line 23' into the synthesis gas stream after the compressor 12, into a line 24. The hydrogen-poor stream 22 is sent to the burners in the steam reformer 4 as fuel.

Line 24 carries the synthesis gas stream from the compressor 12 to an additional flow reactor 25 for production of methanol. This synthesis gas stream in line 24 is enriched with hydrogen from line 23 or 23'.

The reactor 25 will normally give a yield of around 30% methanol, i.e. around 30–35% of the carbon entering the reactor is converted to methanol. The product stream from the reactor 25 is separated in a crude methanol separator 33, into a methanol-rich stream 27 and a stream 26 consisting mainly of non-reacted synthesis gas and gases that are inert in the methanol synthesis. Stream 26 is passed through a re-circulation compressor 34 in the re-circulation loop 16, and is introduced into the existing reactor 14. Alternatively, if the pressure in line 26 is or is set sufficiently high, stream 26 may as indicated at 26b be led past compressor 34 and directly to the re-circulation loop and the reactor 14.

While the stoichiometric number, SN, for the synthesis gas in line 9 will normally be around 2.06, SN in line 24 will normally be greater than 2.06 due to the addition of hydrogen-rich gas from line 23 or 23'. The methanol-poor stream 26 has a high content of hydrogen compared with other reactive gases, i.e. a high SN that will normally be higher than 2.10.

In order to reduce the SN of the gas from line 26, the re-circulation line 16 is also supplied with a synthesis gas with a lower SN, produced in a separate secondary synthesis gas line 28, 29, 30, 31, 32, 37. This secondary synthesis gas line comprises an ATR or POX reactor 30 that receives oxygen in the form of nearly pure O$_2$, oxygen-enriched air or air via line 29 from oxygen unit 28 and natural gas from line 31. The reactor 30 may alternatively be a steam reformer that is supplied with energy in the form of heat from other processes. It is also possible to use a combination of steam reforming and ATR/POX as reactor 30.

The synthesis gas from this new synthesis gas line is introduced into re-circulation line 16 immediately upstream of the reactor 14, through line 42. This secondary synthesis gas line may also contain units such as compressors and heat exchangers etc. (not shown).

The gas fed to the reactor 30 is pre-treated in the same manner as the original synthesis gas line 2, 4, 8. The excess heat from the process may be used in the various separation stages, or the natural gas feed to ATR or POX 30 may optionally be heated by means of an additional incinerator (fire heater) or heat exchange with hot synthesis gas exiting the ATR or POX 30.

It is also possible to envisage a combination of pre-heating and steam reforming in a convective reformer upstream of the ATR or POX 30.

A pre-converter 37 may optionally be installed in the new synthesis gas line. The pre-converter 37 is supplied with feed gas through line 32. The pre-converter 37 corresponds to the above mentioned converter 25. The flow from the pre-converter 37 is separated into a methanol-rich stream 41 that is passed to the crude methanol separator 13, and a methanol-poor stream 42 that is led to the synthesis loop immediately upstream of the existing reactor 14.

In order to give the correct stoichiometric relationship between the base materials that are fed to the pre-converter 37, a stream 39 is taken off from lines 11 and 9 respectively, and also a stream 38 from the synthesis loop 16, where both streams 38 and 39 are introduced into line 32. The volume of gas drawn out in lines 38 and 39 respectively, depends on the stoichiometric relationship in the gas from the reformer 30 and the desired stoichiometric relationship in the gas fed to the pre-reformer 37.

It is important for the methanol-poor stream 42 to give a synthesis gas with an SN of less than 2, and for this to be introduced in an amount sufficient for the SN of the feed to the synthesis reactor 14 to be reduced to around 2.06 from an SN of more than 2.10 in the gas in line 26.

The flow reactor 25 and the pre-converter 37 are normally flow reactors of the simplest possible type, i.e. of the isothermal tubular reactor type as mentioned above with reference to reactor 14, and will on the outside of the reactor tubes produce more than enough steam at the correct pressure to achieve a favourable ratio between steam and carbon into the reformer. Normally, 30 to 40% of the steam generated on the outside of the tubes in reactor 25 in order to cool this is used as feed to the new reformer 30 in order to achieve the desired ratio of steam/carbon therein. The remainder of the steam may be used in other steam and/or heat-requiring processes such as e.g. purification/after-treatment of the methanol stream. The methanol-rich product stream typically contains around 15% water and some ethanol, and therefore a distillation is normally carried out in order to obtain pure methanol.

The conversion in the new reactors 25 and 37 will affect the conversion in the existing synthesis reactor 14, so that a reduced conversion in the reactors 25 and 37 will lead to more unconverted synthesis gas being introduced from the reactors 25 and 37 to the synthesis reactor 14, causing the methanol production in 14 to increase. The reactors 25 and 37 themselves will also produce the product, thus contributing to an increase in capacity for the plant. It is important to adjust the conversion in the reactors 25 and 77 so that the stoichiometry of the gas fed to the synthesis reactor 14 is optimally tailored for an efficient synthesis of the product, while maximising the overall conversion of synthesis gas to product.

The amount of gas taken off from re-circulation line 16 as purge gas through line 19 and how much is re-circulated straight back in line 16 to the synthesis reactor 14, may be varied for optimisation of the system

EXAMPLES

The table below shows simulation results for two examples, one for an existing methanol process according to the drawing in FIG. 1, and one for a plant according to the present invention.

The basis for the simulation is natural gas with a methane content of approximately 82%. The oxygen feed has been varied, so that the $CH_4$-slip is approximately 1.36%. The admissions of the existing reformer section is the same for both examples.

The new ATR operates at 35 bar and the ratio of steam to carbon (S/C) into the pre-reformer in the new line II is 1.0. The flow reactor 25 is positioned after the synthesis gas reactor 12, and has an outlet pressure of 80 bar.

|  |  | Example 1 Existing methanol process | Example 2 New concept for increased methanol production |
|---|---|---|---|
| Line I |  |  |  |
| NG-rate to existing line | Normalised (%) | 100 | 100 |
| NG-fuel | % | 100 | 100 |
| Oxygen to secondary reformer 8 | % | 100 | 110 |
| S/C in feed to reformers 4, 8 | % | 1.8 | 1.8 |
| Temperature of primary reformer 4 |  |  |  |
| Duty | % | 100 | 100 |
| Temperature of secondary reformer 8 | ° C. | 1000 | 1000 |
| Line II |  |  |  |
| NG-rate to ATR-line 31 | % relative to existing plant |  | 26 |
| S/C-feed to new pre-reformer |  |  | 1 |
| Oxygen to new ATR 30 | % relative to existing plant |  | 40 |
| Inlet temperature of new ATR 30 | ° C. |  | 600 |
| Outlet temperature of new ATR 30 | ° C. |  | 1000 |
| Outlet pressure from new ATR 30 | bara |  | 35 |
| $CH_4$-slip from new ATR 30 | mole % |  | 1.4 |
| Stoichiometric numbers |  |  |  |
| SN 1, line I from pre-reactor |  |  | 2.13 |
| SN 2, line I, feed for pre-reactor |  |  | 2.08 |
| SN 4, line II from new ATR 30 |  |  | 1.68 |
| SN fra CR, line 9 |  |  | 2.02 |
| SN 3, line I + II, MUG to synthesis loop |  |  | 2.06 |
| Synthesis loop |  |  |  |
| Re-circulation ratio in synthesis loop |  | 4.2 | 4.2 |
| Overall consumption and production |  |  |  |
| Overall NG to main process | % | 100 |  |
| Overall $O_2$ consumption | % | 100 |  |
| Overall production of crude methanol, I + II (methanol content in crude methanol) | % | 100 | 126 |

The table shows that in this example, the production of crude methanol in a process plant for methanol production may be increased substantially without straining the original plant more than for conventional operation. Above all, this is significant when it comes to expansion of existing plants where it is desirable to make the greatest possible use of existing plants without needing to re-dimension and modify large parts of the existing plant.

For the modified plant, it is possible to make use of excess materials or non-converted quantities of a type of reactants in the process by introducing new quantities of other reactants, thus increasing the production so as to make it less expensive.

It may be important to note that the individual modules and components of the exemplified plants may be constructed differently from that which is originally seen in the figures. Elements that those skilled in the art know form part or may form part of such plants, e.g. heat exchangers, compressors, flash tanks etc., have in part been omitted, as they are not significant to the invention. Likewise, the combination of the different elements may differ. Thus some of the elements drawn as one unit may consist of several identical or different elements connected in series and/or in parallel. As an example, the reactor 14 may comprises a plurality of reactors connected in parallel and/or in series.

The present method and process plant are also applicable to the expansion of plants for production of oxygenated hydrocarbons other than methanol, such as e.g. dimethyl ether. A plant for production of dimethyl ether has a construction and principle of operation that are relatively similar to those of a methanol production plant, and as such the problems are parallel. Although the invention has been written with reference to a plant for production of methanol, it also covers other plants as mentioned above.

The invention claimed is:

1. A method of increasing the production in an existing process plant for converting natural gas into a product, comprising:
   converting the natural gas to a synthesis gas in a synthesis gas section, the synthesis gas being brought to reaction in a first reactor for synthesis of the product;
   separating non-converted synthesis gas and product into two streams, wherein a product-rich stream is taken off the process, and a product-poor stream is re-circulated back as feed to the first reactor together with fresh synthesis gas;
   taking part of the product-poor stream off a re-circulation loop as a purge gas;
   separating the purge gas into hydrogen-rich and hydrogen-poor streams, where the hydrogen-rich streams are introduced in stages of the process where addition of hydrogen is desirable, and where the residual thermal value of the hydrogen-poor stream may be used for heating prior to the stream being discharged;
   wherein the synthesis gas from the synthesis gas section receives a first hydrogen-rich stream from the separated purge gas to form a hydrogen enriched synthesis gas;
   passing the hydrogen enriched synthesis gas through a second reactor for production of product, and also a unit for separating a second product-rich stream that is taken off, and a second product-poor stream used as feed to the first reactor;
   wherein the second product-poor stream, which is used as feed to the first reactor, receives additional synthesis gas produced in a separate secondary synthesis gas line comprising a pre-converter.

2. The method according to claim 1, wherein the separate secondary synthesis gas line comprises a steam reformer.

3. The method according to claim 1, wherein the stream from the pre-converter is separated into the second product-rich stream that is passed to a section for product purification, and the second product-poor stream that is introduced to a synthesis loop upstream the first reactor.

4. The method according to claim 2, wherein the stream from the pre-converter is separated into the second product-rich stream that is passed to a section for product purification, and the second product-poor stream that is introduced to a synthesis loop upstream the first reactor.

5. The method according to claim 3, wherein at least one of hydrogen enriched synthesis gas from the synthesis gas section and gas from the re-circulation loop in the synthesis section is taken off and introduced into the secondary synthesis gas line upstream of the pre-converter.

6. The method according to claim 4, wherein at least one of hydrogen enriched synthesis gas from the synthesis gas section and gas from the re-circulation loop in the synthesis section is taken off and introduced into the secondary synthesis gas line upstream of the pre-converter.

7. The method according to claim 1, wherein the product is selected from the group consisting of methanol and dimethyl ether.

8. The method according to claim 2, wherein the product is selected from the group consisting of methanol and dimethyl ether.

9. The method according to claim 3, wherein the product is selected from the group consisting of methanol and dimethyl ether.

10. The method according to claim 4, wherein the product is selected from the group consisting of methanol and dimethyl ether.

11. The method according to claim 5, wherein the product is selected from the group consisting of methanol and dimethyl ether.

12. The method according to claim 6, wherein the product is selected from the group consisting of methanol and dimethyl ether.

13. A process plant for producing a product based on natural gas, comprising:
   a synthesis gas section for production of synthesis gas consisting mainly of CO, $CO_2$, $H_2$ and water;
   a synthesis section in which the product is formed;
   a purification section in which the product is separated from non-converted reactants and other materials and purified, where non-converted reactants separated from the product are re-circulated to the synthesis section, and where part of the re-circulated gas is taken off in a line in order to prevent build-up of inert gases;
   a separation unit for separating the gas taken off in line into hydrogen-rich and hydrogen-poor fractions;
   optionally, a line for leading hydrogen-poor fractions to combustion;
   lines for leading hydrogen-rich fractions into the natural gas feed and to re-circulation to the synthesis section, respectively;
   a flow reactor for synthesis of the product arranged between the synthesis gas section and the synthesis section;
   a separation unit for separation of a product-rich fraction to a line and a product-poor fraction to a line leading to the synthesis section;
   a separate secondary synthesis gas line for production of a secondary synthesis gas, the secondary synthesis gas line comprising a pre-converter; and
   a line for carrying the secondary synthesis gas as feed for the synthesis section.

14. The process plant according to claim 13, wherein the secondary synthesis gas line comprises a steam reformer.

15. The process plant according to claim 13, wherein the pre-converter with an outlet for a product-rich stream that is passed to a product purification section and an outlet for a product-poor stream that is introduced into an original synthesis loop immediately upstream of a reactor of the synthesis section.

16. The process plant according to claim 14, wherein the secondary synthesis gas line comprises a pre-converter with an outlet for a product-rich stream that is passed to a product purification section and an outlet for a product-poor stream that is introduced into the original synthesis loop immediately upstream of a reactor of synthesis.

* * * * *

UNITED STATES PATENT AND TRADEMARK OFFICE
CERTIFICATE OF CORRECTION

PATENT NO. : 7,037,948 B2  Page 1 of 9
APPLICATION NO. : 10/481925
DATED : May 2, 2006
INVENTOR(S) : Hansen et al.

It is certified that error appears in the above-identified patent and that said Letters Patent is hereby corrected as shown below:

Please delete the patent in its entirety and insert the patent 7,037,948 as attached.

Signed and Sealed this
Twenty-second Day of November, 2011

David J. Kappos
*Director of the United States Patent and Trademark Office*

(12) United States Patent
Hansen et al.

(10) Patent No.: US 7,037,948 B2
(45) Date of Patent: *May 2, 2006

(54) METHOD FOR INCREASING THE PRODUCTION IN AN EXISTING PROCESSING PLANT AND A PROCESSING PLANT

(75) Inventors: Roger Hansen, Trondheim (NO); Jostein Sogge, Stjordal (NO); Bjorn Jarle Veland, Jar (NO); Ola Olsvik, Hundhamaren (NO)

(73) Assignee: Statoil ASA, Stavanger (NO)

( * ) Notice: Subject to any disclaimer, the term of this patent is extended or adjusted under 35 U.S.C. 154(b) by 39 days.

This patent is subject to a terminal disclaimer.

(21) Appl. No.: 10/481,925

(22) PCT Filed: Jun. 27, 2002

(86) PCT No.: PCT/NO02/00235

§ 371 (c)(1),
(2), (4) Date: Apr. 26, 2004

(87) PCT Pub. No.: WO03/002497

PCT Pub. Date: Jan. 9, 2003

(65) Prior Publication Data

US 2004/0198846 A1  Oct. 7, 2004

(30) Foreign Application Priority Data

Jun. 27, 2001  (NO) .................. 2001 3226

(51) Int. Cl.
*C07C 27/00* (2006.01)
(52) U.S. Cl. ........ 518/705; 518/700; 518/702; 518/703; 518/704; 518/706
(58) Field of Classification Search ............... 518/700, 518/702, 703, 704, 705, 706
See application file for complete search history.

(56) References Cited

U.S. PATENT DOCUMENTS 6,333,014 B1 *  12/2001  Filippi .................. 423/359
6,794,418 B2 *   9/2004  Sogge et al. ............ 518/706

FOREIGN PATENT DOCUMENTS

WO   WO 01/47846 A1 *  7/2001

* cited by examiner

*Primary Examiner* — J. Parsa
(74) *Attorney, Agent, or Firm* — Kirkpatrick & Lockhart Nicholson Graham LLP (57) ABSTRACT

A method is described for increasing the production in an existing process plant for converting natural gas to a product, wherein the synthesis gas from the synthesis gas section receives a hydrogen-rich stream from the separated purge gas, and that this hydrogen enriched synthesis gas is passed through a new flow reactor for production of product, and also a unit for separating a product-rich stream that is taken off, and a product-poor stream used as feed to the original reactor, and that the product-poor stream, which is used as feed to the original reactor, receives additional synthesis gas produced in a separate secondary synthesis gas line.

16 Claims, 2 Drawing Sheets

METHOD FOR INCREASING THE PRODUCTION IN AN EXISTING PROCESSING PLANT AND A PROCESSING PLANT

CROSS REFERENCE TO RELATED APPLICATIONS

This application is based on International Application No. PCT/N002/00235, filed 27 Jun. 2002, having an International Publication No. of WO 03/002497 A1 and an International Publication Date of 9 Jan. 2003, which is based on Norwegian Patent Application No. 2001 3226, filed 27 Jun. 2001.

FIELD OF INVENTION

The present invention concerns a method of increasing the production in an existing process plant, and a process plant that has been modified in order to implement the method.

DESCRIPTION OF THE INVENTION BACKGROUND

Today, there is a clear tendency when building new process plants such as plants for production of methanol from natural gas or other suitable carbon sources, to build plants with increasingly greater production capacity, e.g. of more than 5000 tons of methanol per day. By so doing, the production costs are reduced due to scale factors.

In areas with a low price on natural gas, methanol may be produced at a cost of down to USD 80 per ton, which allows methanol to gain entry to a fuel market, i.e. to fuel cell cars and electric power production.

For existing process plants that are too small according to today's requirements, there is a demand for solutions whereby the total production may be increased, thus reducing the production costs pr. unit, without having to carry out major, expensive alterations and replacements of the existing process plant.

Methods of producing methanol are known from prior art, which make it possible to achieve a simpler and more reasonable plant, an increased yield or a certain increase in production when compared with a conventional methanol production plant.

Thus EP 849 245 concerns a method of producing methanol, which method makes it possible to use a simpler and more reasonable plant for which the building costs may be reduced considerably; and also a plant for implementing the method. The method and plant described therein correspond in the main to a plant indicated in FIG. 1 in the present application. The re-circulation line 16 appears to have been omitted, as the parameters during the synthesis of methanol are controlled so as to give the maximum conversion to methanol with one pass through the reactor. However, this publication does not describe a method that enables the capacity of existing plants to be increased.

U.S. Pat. No. 4,226,795 regards a method of producing methanol by using purge gas from another process as a raw material or as part of the raw material. A preferred process for supplying purge gas to this method is a high pressure methanol process. Here, the aim is to increase the yield instead of using the purge gas as fuel. This publication does not describe a method that enables the capacity of an existing plant to be increased either.

EP 802 893 on the other hand, regards a method of producing methanol, which according to the introductory part of the specification will allow a considerable increase of the production in an existing plant. However, what is described here, is a plant comprising two synthesis loops for methanol connected in series. Purge gas from the first loop is used as a feed gas for the second synthesis loop. As with the above, this may provide an increased yield. An increased flow through the first synthesis loop can increase the flow of purge gas, and thereby the feed to the second loop. This publication appears to concern an improvement of the method according to U.S. Pat. No. 4,226,795, and can not be used to increase the capacity of an existing plant.

SUMMARY OF THE INVENTION

Thus it is an object of the present invention to provide a method of increasing the production of an existing plant without having to carry out major, expensive alterations of the existing plant; and also a process plant that has been modified in order to implement the present method.

This is achieved according to the present invention by a method of increasing the production of an existing process plant for conversion of natural gas into a product, where the natural gas is first converted into a synthesis gas in a synthesis gas section, the synthesis gas is brought to react in a reactor for synthesis of the product, where non-converted synthesis gas and product are separated into two streams, where a product-rich stream is drawn out of the process, while a product-poor stream is re-circulated back as feed to the reactor along with fresh synthesis gas, and where part of the re-circulating stream is taken off the re-circulation loop as a purge gas, where the purge gas is separated into hydrogen-rich and hydrogen-poor streams, where hydrogen-rich streams are introduced in stages of the process where the addition of hydrogen is desirable, and where the residual thermal value of the hydrogen-poor stream may be used for heating prior to discharge, where the synthesis gas from the synthesis gas section receives a hydrogen-rich stream from the separated purge gas, and that this hydrogen enriched synthesis gas is passed through a new flow reactor for production of the product and a unit for separation of a product-rich stream that is taken off, and a product-poor stream that is used as feed to the original reactor, and that the product-poor stream used as feed to the original reactor receives additional synthesis gas produced in a separate secondary synthesis gas line.

According to a preferred embodiment, the separate secondary synthesis line comprises a steam reformer.

According to another preferred embodiment, the new synthesis gas line also comprises a pre-converter, and that the flow from the pre-converter is separated into a product-rich fraction that is passed to a section for purification of the product, and a product-poor stream that is introduced into the original synthesis loop.

Preferably, hydrogen enriched synthesis gas from the original synthesis gas section and/or gas from the re-circulation loop in the original synthesis section is drawn off and introduced into the new synthesis gas line upstream of the pre-converter.

Preferably, the product produced through the method is methanol or dimethyl ether.

A process plant is also provided for production of a product based on natural gas, where the process plant comprises a synthesis gas section for production of synthesis gas consisting mainly of CO, $CO_2$, $H_2$ and water, a synthesis section in which the product is formed, and also a purification section in which the product is separated from non-converted reactants and other materials and purified, where non-converted reactants that are separated from the product are re-circulated to the synthesis section, and where some of the re-circulated gas is taken off in a line in order to prevent accumulation of inert gases, the plant also comprising a separation unit for separating the gas that is taken off in a line, into hydrogen-rich and hydrogen-poor fractions, a line for optionally leading hydrogen-poor fractions to combustion and lines for leading hydrogen-rich fractions into the natural gas feed and for re-circulation to the synthesis section, respectively, where a flow reactor is disposed between the synthesis gas section and the synthesis section for synthesis of the product, and also a separation unit for separation of a product-rich fraction to a line and a product-poor fraction to a line leading to the synthesis section, and a separate secondary synthesis gas line is provided for production of secondary synthesis gas, along with a line for feeding the secondary synthesis gas to the synthesis reaction.

Preferably, the secondary synthesis gas line comprises a steam reformer.

Preferably, the secondary synthesis gas line also comprises a pre-converter with an outlet for a product-rich stream that is passed to a purification section for the product, and an outlet for a product-poor stream that is introduced into the original synthesis loop upstream of the reactor.

BRIEF DESCRIPTION OF THE DRAWINGS

Below, the invention will be described by means of an example and the accompanying figures, in which:

FIG. 1 schematically shows the construction of a conventional plant for production of methanol from natural gas; and FIG. 2 schematically shows the construction of a plant according to the present invention.

DETAILED DESCRIPTION OF THE PREFERRED EMBODIMENTS

In the main, production of methanol today is carried out in accordance with the schematic drawing in FIG. 1. The process plant consists principally of three sections; a synthesis gas section (2, 4, 8) in which synthesis gas is produced, normally based on natural gas (NG), a synthesis section (14) in which the actual synthesis of methanol takes place, and a distillation section (17) in which the produced methanol is purified. The synthesis of methanol takes place through the two following reactions:
1) $CO+2H_2=CH_3OH$, or
2) $CO_2+3H_2=CH_3OH+H_2O$ The synthesis gases, which mainly comprise $CO$, $CO_2$ and $H_2$, besides water and non-reacted hydrocarbons, are produced according to one of three different concepts, i.e.:
a) conventional steam reforming,
b) conventional autothermal reforming with a catalyst (ATR) or without a catalyst (POX), or
c) a combination of a) and b).

Prior to the natural gas being passed into line 1 to the reformer for synthesis gas production, sulphur compounds are removed in a conventional manner, and steam is then saturated into and/or added directly to the gas. The saturation may also take place through use of a so-called "saturator". Ordinarily, the gas is also treated in a so-called pre-reformer 2 prior to being passed into the reformer 4, 5, in order to convert all higher hydrocarbons.

The following chemical reactions take place during the production of synthesis gas:
3. $CH_4+H_2O=CO+3H_2$, steam reforming
4. $CH_4+1,5O_2=CO+2H_2O$, partial oxidation
5. $CO+H_2O=CO_2+H_2$, shift reaction Reactions 3 and 5 in the reforming reactor are highly endothermic, and the heat required for the reaction may be supplied either through external heating, such as in a steam reformer, or through a combination with partial oxidation according to reaction 4, such as in an autothermal reformer.

In a steam reformer (SR), natural gas (NG) (methane) is converted in a tubular reactor at high temperature and relatively low pressure. A conventional steam reformer consists of a large number of reactor tubes, normally 100 to 1000, with a length of 10–16 m, where each tube has an inner diameter of around 10 cm and an outer diameter of around 12 cm. This unit may have a length of up to 50 meters, a width of more than 10 meters and a height of more than 20 meters, and therefore such a reactor may be relatively space-requiring.

Conventional steam reformers operate in a pressure range from around 15 to 40 bar. The outlet temperature of such a reformer may be close on 950° C. The heat required to drive the reaction is added by means of external heating, and the reformer may be top, bottom or terrace fired. The heat may also be transferred to the reaction by means of convective heat such as in a heat exchanger reactor. The ratio between steam and carbon is from 1.6 to 4, and the ratio between $H_2$ and $CO$ in the product stream from the reformer is around 3. A typical synthesis gas from a conventional steam reformer contains around 3 volume % methane.

In an autothermal reformer (ATR), the synthesis gas production takes place mainly via reactions 3 and 4, so that the heat required for reaction 3 is generated internally by reaction 4. In an ATR, natural gas (methane) is led into a combustion chamber together with oxygenous gas such as air. The temperature of the combustion chamber may reach more than 2000° C. Following the combustion, the reactions are brought into equilibrium across a catalyst before the gases leave the reformer at a temperature of around 1000° C. The dimensions of an ATR may be a height of 10–20 meters with a diameter of around 4–7 meters.

An alternative autothermal reformer makes use of a concept called partial oxidation (POX). Such a reformer does not contain any catalyst for accelerating the reactions, and as such will generally have larger dimensions than an ATR.

Reforming of natural gas may also occur through combined reforming (CR), where the reformer section consists of an SR and an ATR. Combining SR and ATR makes it possible to regulate the composition exiting the reformer section by controlling the admission of the two reformers. In CR, SR is operated at somewhat milder conditions than in the case of normal SR, i.e. at a slightly lower temperature. This results in a slightly higher methane content in the emissions from the reformer. This methane content is converted in the subsequent ATR. For such a reformer, the ratio between carbon and steam lies in the range 1.2 to 2.4, with the ratio between hydrogen and CO in the product gas being well over 2. The optimum stoichiometric number $(SN=(H_2-CO_2)/(CO_2+CO))$ for the synthesis of methanol is around 2.05.

FIG. 1 shows a synthesis gas section of the CR type. However the type of synthesis gas section used in the plant is not critical. A plant with a synthesis gas section of the ATR type will be without SR 4, while a plant of the SR type will have no ATR 8 and air separation unit 7 with associated line 6.

After the synthesis gas section 2, 4, 8, the synthesis gas is carried in line 9 to a heat exchanger 10 in which it is cooled. After the heat exchanger 10, the synthesis gas is carried in line 11 to a compressor 12 in which it is compressed to the desired pressure of the methanol synthesis section, which is typically about 80 bar.

The synthesis of methanol in the synthesis section takes place according to chemical equations 1 and 2 above, and is an exothermic process that traditionally makes use of several different types of reactors 14, such as:

- Isothermal tubular reactor with a catalyst on the inside of vertical tubes and boiling water on the outside. The heat of reaction will then be removed through partial evaporation of the water.
- Adiabatic fixed bed reactors with interstage cooling.
- Fluidized bed reactor.
- Adiabatic reactors with cooling through introduction of new feed at several levels down through the reactor (quench converter system).

After the reactor 14, the product is passed via line 15 to a crude methanol separator 13 that separates the product stream into a methanol-rich stream 40 and a methanol-poor stream 16. The methanol-rich stream in line 40 is passed to a conventional methanol purification unit 17 that produces methanol out of line 18.

The methanol-poor stream is normally passed back to the reactor 14 via a re-circulation line 16. Alternatively, the reactor is a flow reactor without re-circulation, followed by one or more similar reactors connected in series.

FIG. 1 shows a synthesis loop 13, 14, 15 and 16. The actual re-circulation loop consists of a heat exchanger ("inter exchanger") (not shown) that pre-heats the feed to the synthesis reactor and cools the production gas; the synthesis reactor(s) 14; a crude methanol separator 13; and a system for recovering energy from the exothermic methanol synthesis reactions (not shown).

A so-called purge stream is taken off this re-circulation loop via line 19 in order to prevent accumulation of inert (non-reactive) gases in the re-circulation loop. The purge gas in line 19 is often split into a first stream 19a that is brought together with the feed gas in the gas feed 1, and a second stream 19b that is used as fuel gas for heat-requiring processes in the methanol synthesis, such as the steam reformer 4, or in another process in the same plant; or it is discharged.

A drawback of this prior art is that inert gases, primarily nitrogen, in the re-circulated purge gas will react with other components of the synthesis gas and convert to $NO_x$ and $NH_3$ under the high temperatures of the reforming plant. According to the present invention, this is avoided through that part of the purge gas which is rich in inert gas being used only as fuel for energy-requiring processes such as the steam reformer 4.

Improved Process For Synthesis of Methanol

FIG. 2 illustrates a preferred embodiment of the present invention, where a conventional, existing methanol synthesis plant such as described above has been used as a basis, and where this plant has been modified in order to increase the production capacity. A plant with an existing reformer section based on CR was used as a basis.

In this modified plant, equivalent elements have been given the same reference number, and the description is mainly concerned with the differences relative to the original plant.

Purge gas taken off from the re-circulation loop in line 19 is here separated into three streams in a separation unit 20; two hydrogen-rich streams 21, 23 at different pressures, and a hydrogen-poor stream 22. The separation unit 20 is a conventional hydrogen recovery unit that works according to either the Pressure Swing Adsorbtion (PSA)-principle, the membrane principle or is of a cryogenic type. Preferably, the hydrogen-rich fractions have a hydrogen content of 70 to 100%.

One hydrogen-rich stream 21 is led into the gas feed 1 and mixed with the incoming natural gas. The second hydrogen-rich stream 23 is led into the synthesis gas stream in line 11. Alternatively, and depending on the relative pressures of the various parts, this hydrogen-rich stream 23 may be led via line 23' into the synthesis gas stream after the compressor 12, into a line 24. The hydrogen-poor stream 22 is sent to the burners in the steam reformer 4 as fuel.

Line 24 carries the synthesis gas stream from the compressor 12 to an additional flow reactor 25 for production of methanol. This synthesis gas stream in line 24 is enriched with hydrogen from line 23 or 23'.

The reactor 25 will normally give a yield of around 30% methanol, i.e. around 30–35% of the carbon entering the reactor is converted to methanol. The product stream from the reactor 25 is separated in a crude methanol separator 33, into a methanol-rich stream 27 and a stream 26 consisting mainly of non-reacted synthesis gas and gases that are inert in the methanol synthesis. Stream 26 is passed through a re-circulation compressor 34 in the re-circulation loop 16, and is introduced into the existing reactor 14. Alternatively, if the pressure in line 26 is or is set sufficiently high, stream 26 may as indicated at 26b be led past compressor 34 and directly to the re-circulation loop and the reactor 14.

While the stoichiometric number, SN, for the synthesis gas in line 9 will normally be around 2.06, SN in line 24 will normally be greater than 2.06 due to the addition of hydrogen-rich gas from line 23 or 23'. The methanol-poor stream 26 has a high content of hydrogen compared with other reactive gases, i.e. a high SN that will normally be higher than 2.10.

In order to reduce the SN of the gas from line 26, the re-circulation line 16 is also supplied with a synthesis gas with a lower SN, produced in a separate secondary synthesis gas line 28, 29, 30, 31, 32, 37. This secondary synthesis gas line comprises an ATR or POX reactor 30 that receives oxygen in the form of nearly pure $O_2$, oxygen-enriched air or air via line 29 from oxygen unit 28 and natural gas from line 31. The reactor 30 may alternatively be a steam reformer that is supplied with energy in the form of heat from other processes. It is also possible to use a combination of steam reforming and ATR/POX as reactor 30.

The synthesis gas from this new synthesis gas line is introduced into re-circulation line 16 immediately upstream of the reactor 14, through line 42. This secondary synthesis gas line may also contain units such as compressors and heat exchangers etc. (not shown).

The gas fed to the reactor 30 is pre-treated in the same manner as the original synthesis gas line 2, 4, 8. The excess heat from the process may be used in the various separation stages, or the natural gas feed to ATR or POX 30 may optionally be heated by means of an additional incinerator (fire heater) or heat exchange with hot synthesis gas exiting the ATR or POX 30.

It is also possible to envisage a combination of pre-heating and steam reforming in a convective reformer upstream of the ATR or POX 30.

A pre-converter 37 may optionally be installed in the new synthesis gas line. The pre-converter 37 is supplied with feed gas through line 32. The pre-converter 37 corresponds to the above mentioned converter 25. The flow from the pre-converter 37 is separated into a methanol-rich stream 41 that is passed to the crude methanol separator 13, and a methanol-poor stream 42 that is led to the synthesis loop immediately upstream of the existing reactor 14.

In order to give the correct stoichiometric relationship between the base materials that are fed to the pre-converter 37, a stream 39 is taken off from lines 11 and 9 respectively, and also a stream 38 from the synthesis loop 16, where both streams 38 and 39 are introduced into line 32. The volume of gas drawn out in lines 38 and 39 respectively, depends on the stoichiometric relationship in the gas from the reformer 30 and the desired stoichiometric relationship in the gas fed to the pre-reformer 37.

It is important for the methanol-poor stream 42 to give a synthesis gas with an SN of less than 2, and for this to be introduced in an amount sufficient for the SN of the feed to the synthesis reactor 14 to be reduced to around 2.06 from an SN of more than 2.10 in the gas in line 26.

The flow reactor 25 and the pre-converter 37 are normally flow reactors of the simplest possible type, i.e. of the isothermal tubular reactor type as mentioned above with reference to reactor 14, and will on the outside of the reactor tubes produce more than enough steam at the correct pressure to achieve a favorable ratio between steam and carbon into the reformer. Normally, 30 to 40% of the steam generated on the outside of the tubes in reactor 25 in order to cool this is used as feed to the new reformer 30 in order to achieve the desired ratio of steam/carbon therein. The remainder of the steam may be used in other steam and/or heat-requiring processes such as e.g. purification/after-treatment of the methanol stream. The methanol-rich product stream typically contains around 15% water and some ethanol, and therefore a distillation is normally carried out in order to obtain pure methanol.

The conversion in the new reactors 25 and 37 will affect the conversion in the existing synthesis reactor 14, so that a reduced conversion in the reactors 25 and 37 will lead to more unconverted synthesis gas being introduced from the reactors 25 and 37 to the synthesis reactor 14, causing the methanol production in 14 to increase. The reactors 25 and 37 themselves will also produce the product, thus contributing to an increase in capacity for the plant. It is important to adjust the conversion in the reactors 25 and 77 so that the stoichiometry of the gas fed to the synthesis reactor 14 is optimally tailored for an efficient synthesis of the product, while maximizing the overall conversion of synthesis gas to product.

The amount of gas taken off from re-circulation line 16 as purge gas through line 19 and how much is re-circulated straight back in line 16 to the synthesis reactor 14, may be varied for optimization of the system.

EXAMPLES

The table below shows simulation results for two examples, one for an existing methanol process according to the drawing in FIG. 1, and one for a plant according to the present invention.

The basis for the simulation is natural gas with a methane content of approximately 82%. The oxygen feed has been varied, so that the $CH_4$-slip is approximately 1.36%. The admissions of the existing reformer section is the same for both examples.

The new ATR operates at 35 bar and the ratio of steam to carbon (S/C) into the pre-reformer in the new line II is 1.0. The flow reactor 25 is positioned after the synthesis gas reactor 12, and has an outlet pressure of 80 bar.

|  |  | Example 1 Existing methanol process | Example 2 New concept for increased methanol production |
|---|---|---|---|
| Line I |  |  |  |
| NG-rate to existing line | Normalised (%) | 100 | 100 |
| NG-fuel | % | 100 | 100 |
| Oxygen to secondary reformer 8 | % | 100 | 110 |
| S/C in feed to reformers 4, 8 | % | 1.8 | 1.8 |
| Temperature of primary reformer 4 |  |  |  |
| Duty | % | 100 | 100 |
| Temperature of secondary reformer 8 | ° C. | 1000 | 1000 |
| Line II |  |  |  |
| NG-rate to ATR-line 31 | % relative to existing plant |  | 26 |
| S/C-feed to new pre-reformer |  |  | 1 |
| Oxygen to new ATR 30 | % relative to existing plant |  | 40 |
| Inlet temperature of new ATR 30 | ° C. |  | 600 |
| Outlet temperature of new ATR 30 | ° C. |  | 1000 |
| Outlet pressure from new ATR 30 | bara |  | 35 |
| $CH_4$-slip from new ATR 30 | mole % |  | 1.4 |
| Stoichiometric numbers |  |  |  |
| SN 1, line I from pre-reactor |  |  | 2.13 |
| SN 2, line I, feed for pre-reactor |  |  | 2.08 |
| SN 4, line II from new ATR 30 |  |  | 1.68 |
| SN fra CR, line 9 |  |  | 2.02 |
| SN 3, line I + II, MUG to synthesis loop |  |  | 2.06 |
| Synthesis loop |  |  |  |
| Re-circulation ratio in synthesis loop |  | 4.2 | 4.2 |
| Overall consumption and production |  |  |  |
| Overall NG to main process | % | 100 |  |
| Overall $O_2$ consumption | % | 100 |  |
| Overall production of crude methanol, I + II (methanol content in crude methanol) | % | 100 | 126 |

The table shows that in this example, the production of crude methanol in a process plant for methanol production may be increased substantially without straining the original plant more than for conventional operation. Above all, this is significant when it comes to expansion of existing plants where it is desirable to make the greatest possible use of existing plants without needing to re-dimension and modify large parts of the existing plant.

For the modified plant, it is possible to make use of excess materials or non-converted quantities of a type of reactants in the process by introducing new quantities of other reactants, thus increasing the production so as to make it less expensive.

It may be important to note that the individual modules and components of the exemplified plants may be constructed differently from that which is originally seen in the figures. Elements that those skilled in the art know form part or may form part of such plants, e.g. heat exchangers, compressors, flash tanks etc., have in part been omitted, as they are not significant to the invention. Likewise, the combination of the different elements may differ. Thus some of the elements drawn as one unit may consist of several identical or different elements connected in series and/or in parallel. As an example, the reactor 14 may comprises a plurality of reactors connected in parallel and/or in series.

The present method and process plant are also applicable to the expansion of plants for production of oxygenated hydrocarbons other than methanol, such as e.g. dimethyl ether. A plant for production of dimethyl ether has a construction and principle of operation that are relatively similar to those of a methanol production plant, and as such the problems are parallel. Although the invention has been written with reference to a plant for production of methanol, it also covers other plants as mentioned above.

The invention claimed is:

1. A method of increasing the production in an existing process plant for converting natural gas into a product, comprising:
   converting the natural gas to a synthesis gas in a synthesis gas section, the synthesis gas being brought to reaction in a first reactor for synthesis of the product;
   separating non-converted synthesis gas and product into two streams, wherein a product-rich stream is taken off the process, and a product-poor stream is re-circulated back as feed to the first reactor together with fresh synthesis gas;
   taking part of the product-poor stream off a re-circulation loop as a purge gas;
   separating the purge gas into hydrogen-rich and hydrogen-poor streams, where the hydrogen-rich streams are introduced in stages of the process where addition of hydrogen is desirable, and where the residual thermal value of the hydrogen-poor stream may be used for heating prior to the stream being discharged;
   wherein the synthesis gas from the synthesis gas section receives a first hydrogen-rich stream from the separated purge gas to form a hydrogen enriched synthesis gas;
   passing the hydrogen enriched synthesis gas through a second reactor for production of product, and also a unit for separating a second product-rich stream that is taken off, and a second product-poor stream used as feed to the first reactor;
   wherein the second product-poor stream, which is used as feed to the first reactor, receives additional synthesis gas produced in a separate secondary synthesis gas line comprising a pre-converter.

2. The method according to claim 1, wherein the separate secondary synthesis gas line comprises a steam reformer.

3. The method according to claim 1, wherein the stream from the pre-converter is separated into the second product-rich stream that is passed to a section for product purification, and the second product-poor stream that is introduced to a synthesis loop upstream the first reactor.

4. The method according to claim 2, wherein the stream from the pre-converter is separated into the second product-rich stream that is passed to a section for product purification, and the second product-poor stream that is introduced to a synthesis loop upstream the first reactor.

5. The method according to claim 3, wherein at least one of hydrogen enriched synthesis gas from the synthesis gas section and gas from the re-circulation loop in the synthesis section is taken off and introduced into the secondary synthesis gas line upstream of the pre-converter.

6. The method according to claim 4, wherein at least one of hydrogen enriched synthesis gas from the synthesis gas section and gas from the re-circulation loop in the synthesis section is taken off and introduced into the secondary synthesis gas line upstream of the pre-converter.

7. The method according to claim 1, wherein the product is selected from the group consisting of methanol and dimethyl ether.

8. The method according to claim 2, wherein the product is selected from the group consisting of methanol and dimethyl ether.

9. The method according to claim 3, wherein the product is selected from the group consisting of methanol and dimethyl ether.

10. The method according to claim 4, wherein the product is selected from the group consisting of methanol and dimethyl ether.

11. The method according to claim 5, wherein the product is selected from the group consisting of methanol and dimethyl ether.

12. The method according to claim 6, wherein the product is selected from the group consisting of methanol and dimethyl ether.

13. A process plant for producing a product based on natural gas, comprising:
   a synthesis gas section for production of synthesis gas consisting mainly of CO, $CO_2$, $H_2$ and water;
   a synthesis section in which the product is formed;
   a purification section in which the product is separated from non-converted reactants and other materials and purified, where non-converted reactants separated from the product are re-circulated to the synthesis section, and where part of the re-circulated gas is taken off in a line in order to prevent build-up of inert gases;
   a separation unit for separating the gas taken off in line into hydrogen-rich and hydrogen-poor fractions;
   optionally, a line for leading hydrogen-poor fractions to combustion;
   lines for leading hydrogen-rich fractions into the natural gas feed and to re-circulation to the synthesis section, respectively;
   a flow reactor for synthesis of the product arranged between the synthesis gas section and the synthesis section;
   a separation unit for separation of a product-rich fraction to a line and a product-poor fraction to a line leading to the synthesis section;
   a separate secondary synthesis gas line for production of a secondary synthesis gas, the secondary synthesis gas line comprising a pre-converter; and
   a line for carrying the secondary synthesis gas as feed for the synthesis section.

14. The process plant according to claim 13, wherein the secondary synthesis gas line comprises a steam reformer.

15. The process plant according to claim 13, wherein the pre-converter with an outlet for a product-rich stream that is passed to a product purification section and an outlet for a product-poor stream that is introduced into an original synthesis loop immediately upstream of a reactor of the synthesis section.

16. The process plant according to claim 14, wherein the secondary synthesis gas line comprises a pre-converter with an outlet for a product-rich stream that is passed to a product purification section and an outlet for a product-poor stream that is introduced into the original synthesis loop immediately upstream of a reactor of synthesis.

* * * * *